US006921416B2

United States Patent
Khoury (10) Patent No.: US 6,921,416 B2
(45) Date of Patent: Jul. 26, 2005

(54) INTRAOCULAR LENS IMPLANT HAVING ACCOMMODATIVE CAPABILITIES

(76) Inventor: Elie Khoury, 587, Décarie, St-Laurent, Québec (CA), H4L 3L1

( * ) Notice: Subject to any disclaimer, the term of this patent is extended or adjusted under 35 U.S.C. 154(b) by 0 days.

(21) Appl. No.: 10/285,640

(22) Filed: Nov. 1, 2002

(65) Prior Publication Data

US 2003/0083744 A1 May 1, 2003

(30) Foreign Application Priority Data

Nov. 1, 2001 (GB) .............................. 0126234

(51) Int. Cl.[7] .................................... A61F 2/16
(52) U.S. Cl. ...................... 623/6.37; 623/6.22; 623/6.4
(58) Field of Search ................ 623/6.37, 6.22, 623/6.34, 6.32, 6.38, 6.4

(56) References Cited

U.S. PATENT DOCUMENTS

| | | | | | |
|---|---|---|---|---|---|
| 5,522,891 | A | * | 6/1996 | Klaas ........................ | 623/6.37 |
| 5,562,731 | A | * | 10/1996 | Cumming ................... | 606/107 |
| 5,578,081 | A | * | 11/1996 | McDonald ................. | 623/6.17 |
| 5,928,283 | A | * | 7/1999 | Gross et al. .............. | 623/6.34 |
| 6,013,101 | A | * | 1/2000 | Israel ........................ | 623/6.43 |
| 6,533,813 | B1 | * | 3/2003 | Lin et al. ................... | 623/6.37 |
| 6,660,035 | B1 | * | 12/2003 | Lang et al. ................ | 623/6.37 |

FOREIGN PATENT DOCUMENTS

EP 0162573 * 11/1985

* cited by examiner

Primary Examiner—Paul B. Prebilic (57) ABSTRACT

An intraocular implant including a lens and a shell component. The shell component includes a shell peripheral wall encompassing a shell inner volume for protectively enclosing the lens and allowing the latter to move therein between lens accommodating positions. The lens is pivotable within the shell inner volume between a lens first position wherein the lens is in a substantially proximal relationship relative to a shell wall first segment and a lens second position wherein the lens is in a substantially proximal relationship relative to a shell wall second segment. In one embodiment of the invention, the lens peripheral edge defines a lens edge pivot portion and the shell segment joining edge defines a corresponding shell edge pivot portion, the lens and shell edge pivot portion being complementarily configured and sized so that when the lens abuttingly rests against the peripheral wall inner surface, the lens and shell edge pivot portions interact with each other for allowing the lens to pivot between the lens first and second positions.

In another embodiment of the invention, the lens is pivotally suspended within the shell component for pivotal movement between the lens first and second position. In both embodiments, the lens may also pivot to a lens intermediate position in a spaced relationship relative to both the the shell wall first and second segments.

9 Claims, 8 Drawing Sheets

INTRAOCULAR LENS IMPLANT HAVING ACCOMMODATIVE CAPABILITIES

FIELD OF THE INVENTION

The present invention relates to the general field of ophthalmologic devices and is more particularly concerned with an intraocular lens implant having accommodative capabilities.

BACKGROUND OF THE INVENTION

The human eye has three concentric layers of tissue enclosing the lens and the inner media. The eyes outermost covering is the tough, fibrous sclera and its anterior transparent modification, the cornea. The cornea is the major light refractor of the eye. Below the sclera is the pigmented vascular layer of the eye, which includes the choroid, ciliary body and the iris.

The vitreous cavity constitute two-thirds (⅔) of the volume of the eye. It is filled with transparent jell, the vitreous humor. The portion of the eye in front of the vitreous is divided into two compartments, the anterior chamber (between the cornea and iris) and the posterior chamber (between the iris and vitreous). The chambers are filled with aqueous humor. The innermost layer of the eye, or sensory retina, lines the posterior two-thirds (⅔) of the globe and has several distinct histologic layers.

The natural lens of the eye comprises a transparent envelope, called the capsular bag, which contains the crystalline structure and is suspended by the zonules from the surrounding ciliary body. The front and rear walls of the capsular bag are known as interior and posterior capsules, respectively.

The ability of ciliary muscle to contract and the lens to become more convex is called accommodation which increases the ability to see near objects. With increasing age, the lens of every eye undergoes a progressive hardening, with loss of ability to change its shape. Loss of accommodation is manifested by a decreased ability to focus on near objects (commonly referred to as presbyopia), while corrected distance visual acuity remains normal.

Accommodation is thus the natural process by which the lens of the eye can increase the curvature of its front and back surfaces and thereby change its refractive power in order to adjust from distance vision to near vision. This typically occurs in response to contractions of the ciliary muscle.

A cataract is any opacity or discoloration of the lens whether a small, local opacity or the complete loss of transparency.

Clinically, the term cataract is usually reserved for opacities that effect visual acuity. The most common cause of cataract is age related change.

Other causative factors include inflammation, trauma, metabolic and nutritional defects, and radiation damage. Cataracts may develop very slowly over the years or may progress rapidly depending on the cause and the type of cataract.

The cataracts may be in both eyes and, being a progressive condition may cause fading vision and eventual blindness. If a cataract interferes with patient's daily pattern of living, the patient may benefit from cataract extraction, which can be performed using many different surgical techniques.

Cataracts were once surgically removed along with the interior wall of the capsule of the eye. The patient then wore eye glasses or contact lenses which restored vision but did not permit focusing and gave only limited depth perception.

The first implant of a replacement lens within the eye occurred around 1949 and attempted to locate the replacement lens in the posterior chamber of the eye behind the iris. Problems such as dislocation after implantation forced abandonment of this approach, and for some period thereafter intraocular lenses were implanted in the anterior chamber of the eye. Lenses implanted in the anterior chamber of the eye were of various designs.

Others returned to the practice of inserting the lens in the area of the eye posterior to the iris, known as the posterior chamber. This is the area where the patient's natural crystalline lens is located. When the intraocular lens is located in this natural location, substantially normal vision may be restored to the patient and the problem of forward displacement of the vitreous humor and retinal detachment encountered in anterior chamber intraocular lenses are less likely to occur. Many designs of lenses for implantation in the posterior chamber have been proposed. However, most of these designs suffer from lack of sharp variable focusing capability.

The prior art has proposed some examples of lenses of capable of focusing thus offering the wearer the closest possible substitute to the crystalline lens. However, the prior art accommodative lenses suffer from numerous drawbacks including overall complexity leading to increased costs and decreased overall reliability. Accordingly, there exists a need for an improved intraocular lens implant having accommodative capabilities.

SUMMARY OF THE INVENTION

In accordance with an embodiment of the present invention, there is provided an intraocular implanting support for movably supporting a lens and allowing the lens to be implanted within an eye, the lens including a lens body defining a lens first surface, a generally opposed lens second surface and a lens peripheral edge extending substantially peripherally therebetween, the implanting support comprising: a shell component, the shell component including a shell peripheral wall, the shell peripheral wall at least partially encompassing a shell inner volume for protectively receiving the lens and allowing the latter to move therein; a shell-to-lens coupling means extending between the shell component and the lens for coupling the shell component to the lens and allowing the lens to move within the shell inner volume according to a generally predetermined pattern upon movement of the shell component.

Typically, the shell component is provided with at least one haptic extending generally outwardly from the shell peripheral wall. Also, typically, the shell peripheral wall encloses the shell inner volume for protectively separating the external environment located outside the shell peripheral wall.

Conveniently, the shell peripheral wall defines a peripheral wall inner surface, the shell-to-lens coupling means allowing the lens to move within the shell inner volume so as to vary the relative position between the lens and the peripheral wall inner surface. Also, preferably, the shell-to-lens coupling means allows the lens to be pivotally coupled to the shell component within the shell inner volume for pivotal movement therein between lens accommodating positions.

In accordance with one embodiment of the invention, the shell inner volume is at least partially filled with a filling fluid. In accordance with another embodiment of the invention, the shell inner volume is at least partially vacuumed.

Typically, the shell peripheral wall defines a shell wall first segment and a shell wall second segment, the inner surface of both the shell wall first and second segments having a generally concave configuration. Also, typically, the shell second wall segment is provided with an externally concave portion optically in line with the lens when the latter is mounted within the shell component.

Furthermore, typically, the shell first and second wall segments are joined together about a common and generally peripheral shell segment joining edge. Conveniently, the shell first and second wall segments both have a generally cupolaed configuration, the shell first and second wall segments being joined together in a generally opposed relationship relative to each other about a common and generally peripheral shell segment joining edge so as to form a generally externally biconvex and internally biconcave shell peripheral wall.

In one embodiment of the invention, the shell segment joining edge has a generally flattened configuration. In another embodiment of the invention, the shell segment joining edge has a generally pointed cross-sectional configuration Conveniently, the lens peripheral edge is pivotally attached to the shell wall inner surface generally adjacent the shell segment joining edge for allowing the lens to pivot between a lens first position wherein the lens is in a substantially proximal relationship relative to the shell wall first segment and a lens second position wherein the lens is in a substantially proximal relationship relative to the shell wall second segment.

Optionally, the implanting support further comprises a suction limiting means positioned between the lens and the shell component for limiting the suction between the lens and the shell component when the lens is in the lens first or second positions. Typically, the suction limiting means includes a spacing protrusion extending inwardly from at least one of the shell first or second wall segments.

Typically, the shell-to-lens coupling means includes at least one coupling arm pivotally attached between the lens and the shell wall inner surface. Also, typically, the coupling arm is pivotally attached to the lens by a first arm pivotal link and the coupling arm is pivotally attached to the shell wall inner surface by a second arm pivotal link. Optionally, the coupling arm is made out of a substantially resiliently deformable material.

Typically, an abutment tongue protrudes inwardly into the shell inner volume from a predetermined quadrant of the shell second wall segment adjacent the shell segment joining edge. In one embodiment of the invention, the shell second wall segment defines a shell recessed section located generally in register with the abutment tongue wherein the shell second wall segment is inwardly recessed.

Conveniently, the shell segment joining edge defines an intercepting geometrical plane generally intercepting the latter, the abutment tongue defining an abutment surface, the abutment surface defining an abutment geometrical plane, the abutment geometrical plane extending at an intercepting-to-abutment plane angle relative to the intercepting geometrical plane. Typically, the intercepting-to-abutment plane angle is such that the intercepting geometrical plane intercepts the abutment geometrical plane within the shell inner volume.

In one embodiment of the invention, the lens peripheral edge is pivotally attached to the shell wall inner surface generally adjacent the shell segment joining edge for allowing the lens to pivot between a lens first position wherein the lens is in a substantially proximal relationship relative to the shell wall first segment and a lens second position wherein the lens is in a substantially proximal relationship relative to the shell wall second segment; the shell-to-lens coupling means including at least one coupling arm pivotally attached between the lens and the shell wall inner surface; the coupling arm being pivotally attached to the lens adjacent a lens coupling region and to the shell wall inner surface respectively by a first arm pivotal link and by a second arm pivotal link; the shell second wall segment being provided with an abutment tongue protruding inwardly into the shell inner volume from a predetermined quadrant of the shell second wall segment adjacent the shell segment joining edge; the shell segment joining edge defining an intercepting geometrical plane generally intercepting the latter, the abutment tongue defining an abutment surface, the abutment surface defining an abutment geometrical plane, the abutment geometrical plane extending at an intercepting-to-abutment plane angle relative to the intercepting geometrical plane; the shell-to-lens coupling means allowing the lens coupling region to be substantially stabilized when the lens is in a lens intermediate position between the lens first and second positions wherein a distal segment of the lens located generally opposite the lens coupling region abuttingly contacts the shell first wall segment.

Typically, the shell-to-lens coupling means allows a portion of the shell-to-lens coupling means to abbutingly contact the abutment surface when the lens is in both the lens second and intermediate positions and to be in a spaced relationship relative to the abutment surface when the lens is in the lens first position.

Also, conveniently, the lens forms a lens geometrical plane substantially bisecting the lens, the implanting support being configured and sized so that the lens geometrical plane is in a substantially parallel relationship with the abutment geometrical plane when the lens is in the lens intermediate position and wherein the lens geometrical plane intercepts the abutment geometrical planer when the lens is in both the lens first and second geometrical planes.

In accordance with another aspect of the present invention, there is also provided an intraocular implant comprising: a lens, the lens including a lens body defining a lens first surface, a generally opposed lens second surface and a lens peripheral edge extending substantially peripherally therebetween; a shell component, the shell component including a shell peripheral wall, the shell peripheral wall defining a peripheral wall inner surface, the shell peripheral wall encompassing a shell inner volume for protectively enclosing the lens and allowing the latter to move therein between lens accommodating positions.

Typically, the lens and shell components are complimentarily configured and sized so as to allow the lens to pivot within the shell inner volume for varying the spacing between the lens first and second surfaces and the peripheral wall inner surface.

Conveniently, the shell peripheral wall defines a shell wall first segment and a shell wall second segment, the shell first and second wall segments both having a generally cupolaed configuration, the shell first and second wall segments being joined together in a generally opposed relationship relative to each other about a common and generally peripheral shell segment joining edge so as to form a generally externally biconvex and internally biconcave shell peripheral wall; the lens being pivotable within the shell inner volume between a lens first position wherein the lens is in a substantially proximal relationship relative to the shell wall first segment and a lens second position wherein the lens is in a substantially proximal relationship relative to the shell wall second segment.

In one embodiment of the invention, the lens peripheral edge defines a lens edge pivot portion and the shell segment joining edge defines a corresponding shell edge pivot portion, the lens and shell edge pivot portion being complementarily configured and sized so that when the lens abuttingly rests against the peripheral wall inner surface, the lens and shell edge pivot portions interact with each other for allowing the lens to pivot between the lens first and second positions.

Optionally, the intraocular implant further comprises a lens stabilizing means for at least partially stabilizing the lens in a lens intermediate position between the lens first and second positions wherein the lens first and second surfaces are both in a spaced relationship respectively relative to the shell wall first and second wall segments. Typically, the lens stabilizing means includes a stabilizing protrusion extending from the shell edge pivot portion.

In one embodiment of the invention, the intraocular implant further comprises a shell-to-lens coupling means extending between the shell component and the lens for coupling the shell component to the lens and allowing the lens to move between the shell first and second positions; the shell-to-lens coupling means includes at least one coupling arm pivotally attached between the lens and the shell wall inner surface.

Conveniently, the coupling arm is pivotally attached to the lens by a first arm pivotal link and the coupling arm is pivotally attached to the shell wall inner surface by a second arm pivotal link.

Typically, an abutment tongue protrudes inwardly into the shell inner volume from a predetermined quadrant of the shell second wall segment adjacent the shell segment joining edge.

Conveniently, the shell segment joining edge defines an intercepting geometrical plane generally intercepting the latter; the abutment tongue defining an abutment surface, the abutment surface defining an abutment geometrical plane, the abutment geometrical plane extending at an intercepting-to-abutment plane angle relative to the intercepting geometrical plane; the shell-to-lens coupling means allowing the lens coupling region to be substantially stabilized when the lens is in a lens intermediate position between the lens first and second positions wherein a distal segment of the lens located generally opposite the lens coupling region abuttingly contacts the shell first wall segment.

Advantages of the present invention includes that the proposed intraocular lens implant is particular well suited for lens replacement during cataract surgery or other types of surgery and is specifically designed so as to emulate the natural process of accommodation.

Furthermore, the proposed intraocular lens is designed so as to provide accommodation over substantial variable range of refractive power. Still further, the proposed intraocular lens implant is specifically designed so as to provide for a transitionally smooth accommodation, the accommodation being performed gradually by gravitational force as the eye of the intended user is tilted.

Still further, the proposed intraocular lens implant is designed so as to reduce interaction with adjacent intraocular structures during accommodation movement thereof. Its accommodation capability is independent of its position inside the eye, or the size of the pupil. Also, the proposed intraocular lens implant is configured so as to reduce the risks of posterior capsule fibrosis, that is fibrosis occurring against the rear section of the implant.

Furthermore the proposed intraocular lens implant is designed so as to reduce friction between the lens and the surrounding medium. Reduction of the friction between the lens and its adjacent medium, in turn, provides a smoother and quicker accommodation.

Still further, the proposed intraocular lens implant is specifically designed so as to be compatible with most modern cataract surgery procedures. Also, the proposed intraocular lens implant is suitable for use of a laser treatment after cataract surgery to open an opacified posterior capsule.

Furthermore, even in situations wherein the capsule is unintentionally ruptured during surgery or thereafter, the proposed implant is designed so as to remain relatively functional. Still furthermore, the proposed implant is designed so as to be manufacturable using conventional forms of manufacturing and conventional materials so as to provide an implant that will be economically feasable, long lasting and relatively trouble free in operation.

BRIEF DESCRIPTION OF THE DRAWINGS

Embodiments of the present invention will now be disclosed, by way of example, in reference to the following drawings, in which.

DETAILED DESCRIPTION

Figure 1:
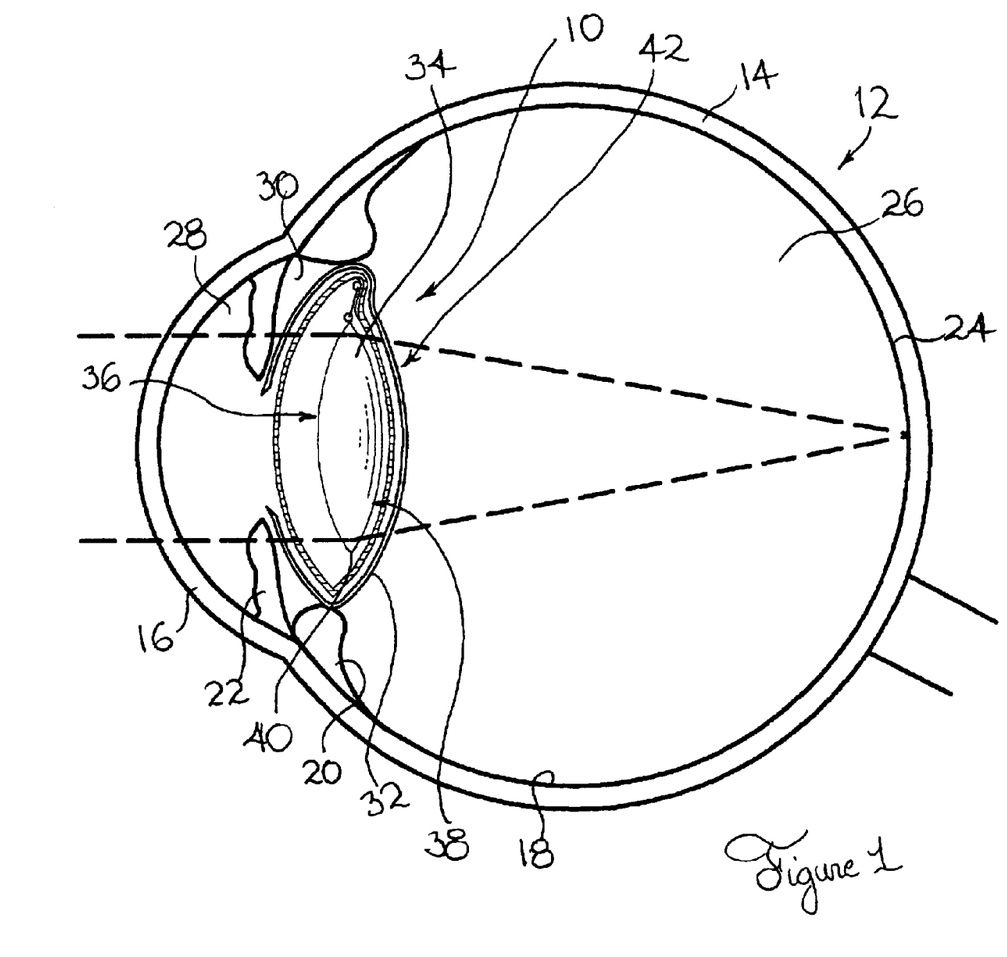
FIG. 1: in a schematic cross sectional view, illustrates an intraocular lens implant in accordance with an embodiment of the present invention, the implant being implanted within a human eye.
Figure 2:
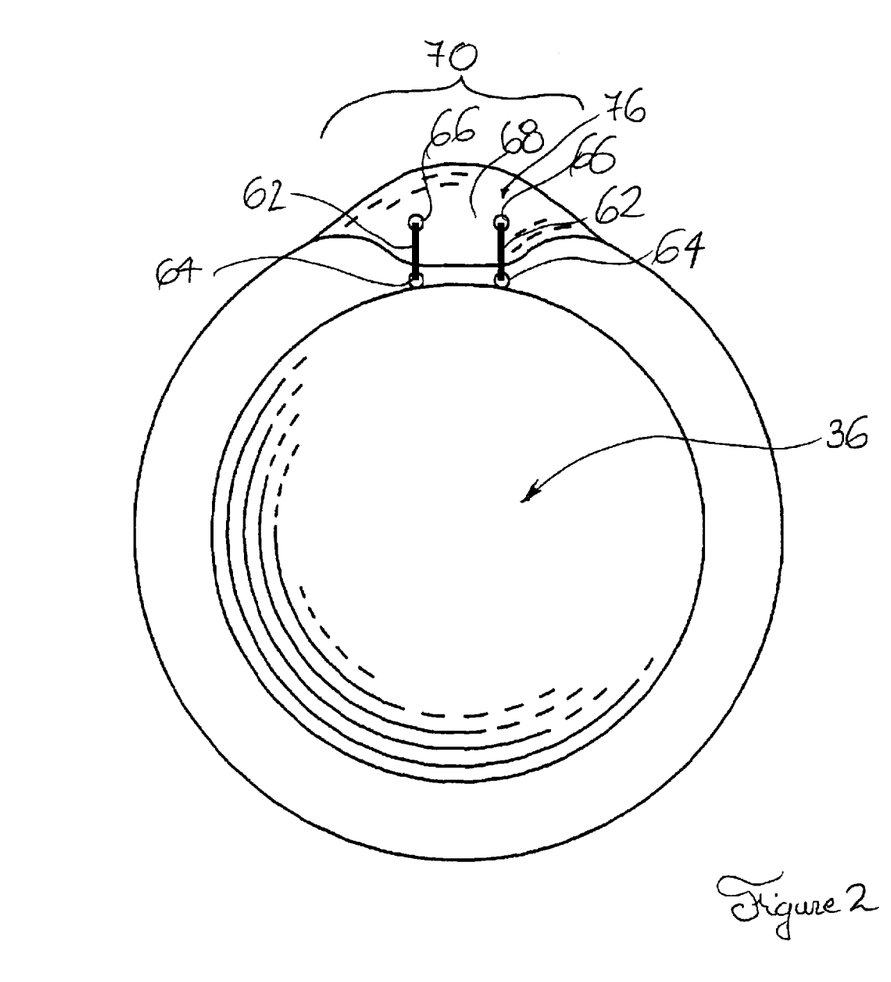
FIG. 2: in a front elevational view, illustrates part of the intraocular lens implant shown in FIG. 1.

Referring to FIG. 1, there is shown an intraocular lens implant (10) in accordance with an embodiment of the present invention. The intraocular lens implant (10) is shown implanted within a schematized human eye (12).

As is well known in the art, the eye (12) has an outermost covering including a fibrous sclera (14) and a cornea (16). A pigmented vascular layer is positioned inwardly relative to the sclera (14). The pigmented vascular layer includes the choroid (18), the ciliary body (20) and the iris (22).

The eye (12) also includes a retina (24) positioned immediately under a pigmented epithelial layer. The eye (12) also includes a vitreous cavity (26) filled with a transparent gel called the vitreous humor.

The portion of the eye (12) located in front of the vitreous cavity (26) is divided into two chambers. An anterior chamber (28) extends between the cornea (16) and the iris (22). A posterior chamber (30) extends between the iris (22) and the vitreous chamber (26). The anterior and posterior chambers (28), (30) are filled with aqueous humor.

It is to be understood that the eye (12) schematically illustrated in FIG. 1 includes only certain basic parts thereof believed to be sufficient to disclose some of the benefits to be derived from the present invention. Typically, zonules (not shown) extend from the ciliary body (20) to a biologically existing capsule or capsular bag (also not shown) having an interior portion or wall frequently termed an anterior capsule and a posterior portion or wall frequently termed a posterior capsule (both of which not shown). As is well known, the zonules typically exert a pulling or tensional force on the capsular bag, causing the latter to assume a more flattened configuration than its usual more spherical shape.

Also, as is well known in the art, cataract removal may be accomplished by various methods. For example, cataract removal may be accomplished by intracapsular extraction, that is removal of the entire length or by extracapsular extraction, that is removal of the cataractous nucleus and cortex through the anterior side of the lens capsular bag. Extracapsular extraction may be performed utilizing either nucleus expression and a relatively large opening in the eye or phacoemulsification and a relatively small opening in the eye. The essentially empty lens capsule remaining after removal of the cataract is referred to as the capsular bag. Removal of the nucleus and cortex of the natural or biological lens from the capsular bag creates a space immediately behind the iris (22) between the latter and the posterior capsule of the bag.

It should be understood that although the intraocular lens (10) is shown in FIG. 1 as being implanted in the posterior chamber (30), the intraocular lens implant (10) is implantable in any of the eye chambers, that is the anterior chamber (28), the posterior chamber (30) or the capsular bag without departing from the scope of the present invention. Also, it should be understood that the intraocular lens implant (10) is designed so as to be implantable within an eye (12) through any suitable method.

The intraocular lens implant (10) typically includes an optical lens (34). The lens (34), in turn, includes a lens body defining a lens first surface (36) and a generally opposed lens second surface (38). The lens body also defines a lens peripheral edge (40) extending substantially peripherally therebetween.

It should be understood that although the lens (34) is shown throughout FIGS. as having a generally biconvex configuration, the lens (34) could have other general configurations such as plano-convex, plano-covex with a planar Fresnel surface, planar with one Fresnel surface, planar with two opposed Fresnel surfaces, concave-convex or other suitable configurations without departing from the scope of the present invention. Also, the lens (34) may be of the single vision or multifocal type or have other suitable optical characteristics without departing from the scope of the present invention. Furthermore, the lens (34) could be made out of PMMA, an other type of polymeric resin or any other suitable material without departing from the scope of the present invention.

The intraocular lens implant (10) also includes an intraocular implanting support (42) for movably supporting the lens (34) and allowing the latter to be implanted within the eye (12). In fact, although the intraocular implanting support (42) is shown throughout the FIGS. as having a lens (34) mounted therein, it should be understood that the intraocular implanting support (42) could be manufactured, used or sold independently of the lens (34) without departing from the scope of the present invention.

In other words, the present invention is concerned both with an intraocular implanting support (42) and with an intraocular implant including both an intraocular implanting support (42) and a lens (34) movably supported thereby. Also, the intraocular implanting support may take any suitable form.

Typically, the intraocular implanting support (42) includes a shell component (44). The shell component (44), in turn, includes a shell peripheral wall (46) at least partially encompassing a shell inner volume (48) for protectively receiving the lens (34) and allowing the latter to move therein. Typically, the lens (34) and the shell component (44) are complimentarily configured and sized so as to allow the lens (34) to pivot within the shell inner volume (48) for varying the spacing between the lens first and second surfaces (36), (38) and the inner surface (50) of the shell peripheral wall (46).

Typically, although by no means exclusively the shell component (46) may be provided with at least one and preferably two haptics (not shown) extending generally outwardly from the shell peripheral wall (46). As illustrated in FIG. 1, the intraocular lens implant (10) may be arranged in the posterior chamber (30) or other suitable chamber while bearing against the margin of the chamber for holding the intraocular lens implant (10) in position. As is well known in the art, the haptic arms, when present, are preferably made out of a generally resiliently deformable material such as a suitable polymeric resin. In FIG. 1, the reference numeral 32 is used to designate the eye lens bag. Said eye lens bag (32) provides the space for the implant (10) and the peripheral wall for contacting the haptic arms.

In accordance with at least one set of embodiments, the intraocular implanting support (42) includes a shell-to-lens coupling means extending between the shell component (44) and the lens (34) for coupling the shell component (44) to the lens (34) and allowing the lens (34) to move within the shell inner volume (48) according to a generally predetermined pattern of movement, upon movement of the shell component (44). The shell-to-lens coupling means hence allows the lens (34) protectively enclosed within the shell inner volume (48) to move therein between lens accommodating positions.

Typically, the shell-to-lens coupling means allows the lens (34) to be pivotally coupled to the shell component (44) within the shell inner volume (48) for pivotal movement therein between lens accommodating positions. Conveniently, the shell peripheral wall (46) encloses the shell inner volume (48) for protectively separating the external environment located outside the shell peripheral wall (46) from the shell inner volume (48).

In at least one embodiment of the invention, the shell inner volume (48) is at least partially filled with a filling fluid. Typically, the shell inner volume (48) is filled with air or another suitable gas in order to reduce frictional drag forces on the lens (34) when the latter moves within the shell inner volume (48). In an alternative embodiment of the invention, the shell inner volume (48) is at least partially vacuumed so as to further reduce frictional drag forces on the lens (34) when the latter moves within the shell inner volume (48).

In the embodiments shown throughout the FIGS., the shell peripheral wall (46) defines a shell wall first segment (52) and a shell wall second segment (54). Also, throughout the FIGS., the inner surface (50) of both the shell wall first and second segments (52), (54) have a generally concave configuration. Again, it should be understood that although the shell component (44) shown throughout the FIGS. has a generally biconvex configuration, the shell component (44) could have other suitable configurations such as planoconvex, concave-convex or any other suitable configurations without departing from the scope of the present invention.

Figure 6:
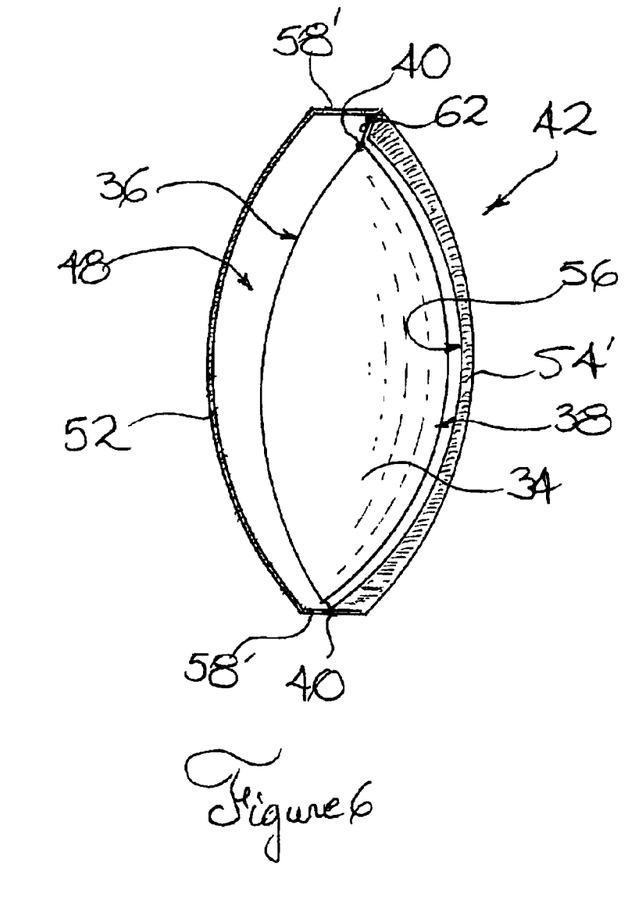
FIG. 6: in a partial cross sectional view with sections taken out, illustrates a intraocular lens implant in accordance with an alternative embodiment of the invention, the lens thereof being shown in a lens second position.
Figure 7:
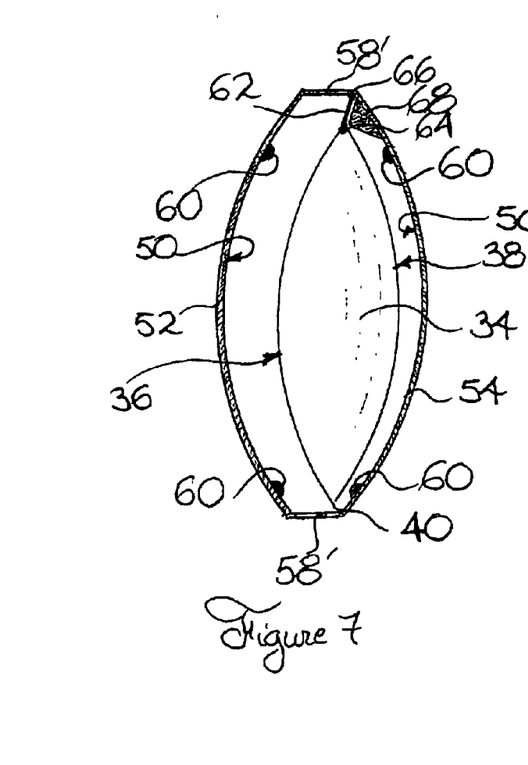
FIG. 7: in a partial cross sectional view with sections taken out, illustrates a intraocular lens implant in accordance with an alternative embodiment of the invention, the lens thereof being shown in a lens second position.
Figure 8:
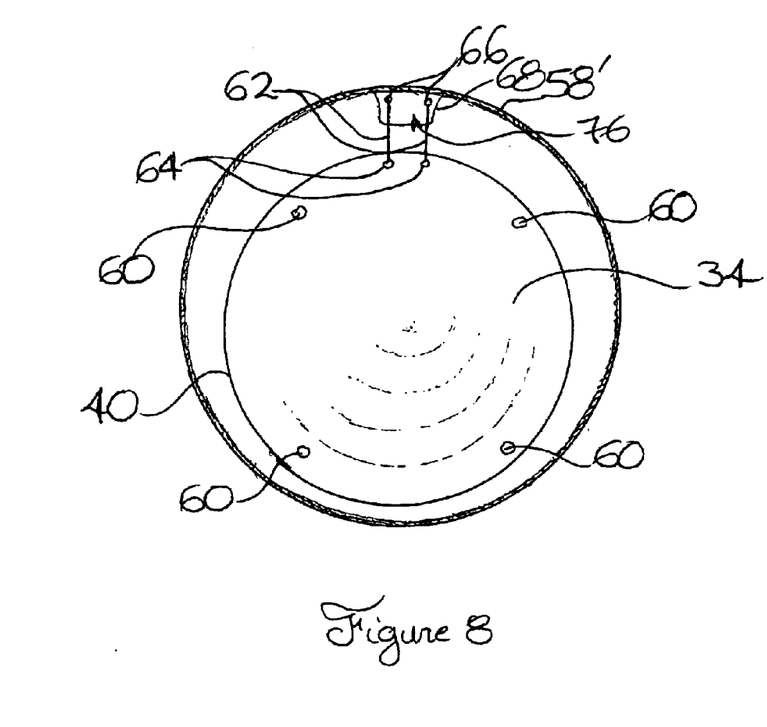
FIG. 8: in a front elevational view illustrates the intraocular lens implant shown in FIG. 7.

For example, as shown more specifically in FIG. 6, the shell second wall segment (54) may be provided with a recessed or concave portion (56). The concave portion (56) is configured, sized and positioned so as to creatre a diverging effect and so as to be generally optically in line with the lens (34) when the latter is mounted within the shell component (44). The concave portion (56) is intended to increase the convergence power of the intraocular implant (10). Accomodation may hence be produced with comparatively less displacement of the lens 34. This may prove to be particularly usefull, for example, with patient having a pronounced myopia.

Typically, the shell first and second wall segments (52), (54) both have a generally cupolaed configuration. The shell first and second wall segments (52), (54) are typically joined together in a generally opposed relationship relative to each other about a common and generally peripheral shell segment joining edge (58). The shell first and second wall segments (52), (54) hence typically form a generally externally biconvex and internally biconcave shell peripheral wall (46).

Although the shell segment joining edge (58) is shown in FIGS. 1 through 5 as having a generally pointed cross sectional configuration, it should be understood that the shell segment joining edge (58) could assume other configurations without departing from the scope of the present invention. For example, as shown in FIGS. 6 through 15, the shell segment joining edge (58') may have a generally flattened cross sectional configuration. The generally flattened cross sectional configuration of the shell segment joining edge (58') may potentially reduce the progression of fibrosis on the posterior capsule behind the intraocular implant (10) and, hence, posterior capsular opacification.

Typically, the lens peripheral edge (40) is pivotally attached to the shell wall inner surface (50) at a position generally adjacent the shell segment joining edge (58). The shell-to-lens coupling means typically allows the lens (34) to pivot between a lens first position, illustrated in FIGS. 5, and 11, wherein the lens (34) is in a substantially proximal relationship relative to the shell wall first segment (52) and a lens second position, illustrated in FIGS. 3 and 9, wherein the lens (34) is in a substantially proximal relationship relative to the shell wall second segment (54). Preferably, the shell-to-lens coupling means allows the lens first surface (36) to be in a generally proximal relationship relative to the shell wall first segment (52) when the lens (34) is in the lens first position and the shell-to-lens coupling means allows the lens second surface (38) to be in a generally proximal relationship relative to the shell wall second segment (54) when the lens (34) is in the lens second position.

Conveniently, the shell-to-lens coupling means allows the lens first and second surfaces to (36), (38) to respectively contact the shell wall first and second segments (52), (54) when the lens (34) is respectively in the first and second lens positions. Also, typically, the interior surface (50) of the shell wall first and second segments (52), (54) is configured and sized so as to substantially complementarily conform respectively to the lens first and second surfaces (36), (38).

In order to reduce potential suction forces between the lens component (34) and the shell wall inner surface (50) that may potentially alter or hinder movement of the lens component (34), the implanting support (42) is optionally provided with a suction limiting means positioned between the lens (34) and the shell component (44) for limiting the suction between the lend (34) and the shell component (44) when the lens (34) is in the lens first or second position. As illustrated more specifically in FIGS. 7 and 8, the suction limiting means may optionally include at least one and typically four symetrically disposed spacing protrusions (60) extending inwardly from the inner surface of at least one and preferably both the shell first and/or second wall segments (52), (54).

In at least one embodiment of the invention, the shell-to-lens coupling means includes at least one coupling arm (62) pivotally attached between the lens (34) and the shell wall (44). Typically, the coupling arm (62) is pivotally attached to the lens (34) by a first arm pivotal link (64) and the coupling arm (62) is pivotally attached to the shell wall inner surface (50) by a second arm pivotal link (66). The coupling arm (62) may take any suitable form. For example, the coupling arm (62) may include a strip of substantially resiliently deformable material such as a suitable elastomeric or polymeric resin. The coupling arm (62) may be made out of a string, a spring or any other generally elongated components. Also, the linking arm (62) may be segmented or assume different configurations without departing from the scope of the present invention. As illustrated more specifically in FIGS. 2 and 8, the shell-to-lens coupling means typically includes two coupling arms (62) positioned in a generally parallel relationship relative to each other. However, the shell-to-lens coupling means may include any suitable number of coupling arms (62) positioned in any suitable configuration relative to each other without departing from the scope of the present invention.

Similarly, the first and second arm pivotal links (64), (66) may take any suitable form. In the embodiments shown throughout the FIGS., the first and second arm pivotal links (64), (66) include linking rings extending from their respective attachment surfaces. However, the first and/or second pivotal links (64), (66) may include attachment apertures, hooks or any other suitable means.

Typically, the implanting support (42) also includes an abutment tongue (68) protruding inwardly into the shell inner volume (48) from a predetermined quadrant (70) of the shell second wall segment (54) adjacent the shell segment joining edge (58). In the embodiments shown throughout the FIGS. 1 through 5, the shell second wall segment (54) also defines a shell recessed section (72) located generally in register with the abutment tongue (68) and wherein the shell second wall segment (54) is inwardly recessed. In the embodiment shown in FIGS. 6 through 15 and more specifically in FIGS. 9 through 11, the shell wall second segment (54) is deprived of the shell recessed section.

Figure 3:
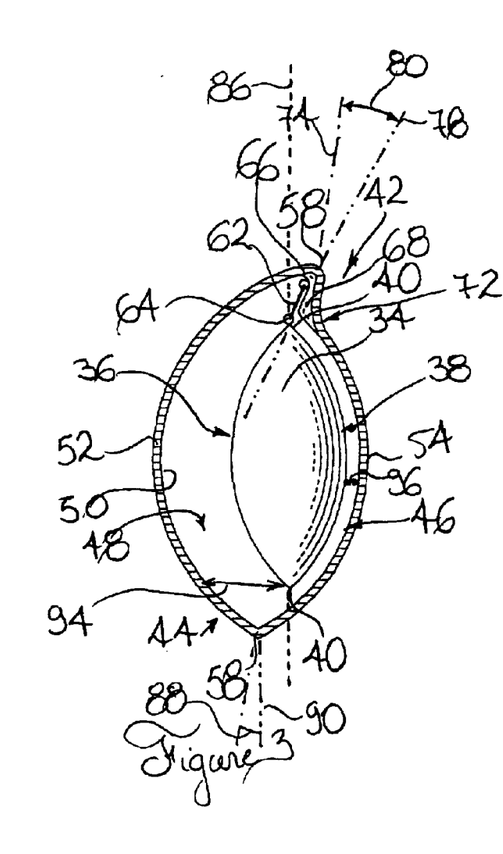
FIG. 3: in a partial cross sectional view with sections taken out, illustrates the intraocular lens implant shown in FIGS. 1 and 2 in a lens second position.
Figure 4:
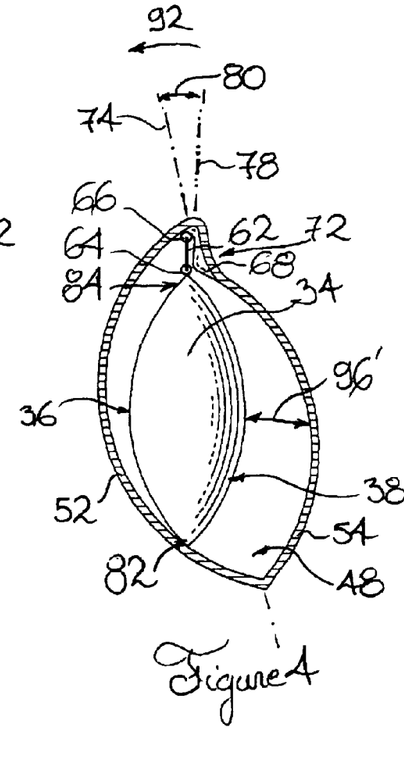
FIG. 4: in a partial cross sectional view with sections taken out, illustrates the intraocular lens implant shown in FIGS. 1 through 3 in a lens intermediate position.
Figure 5:
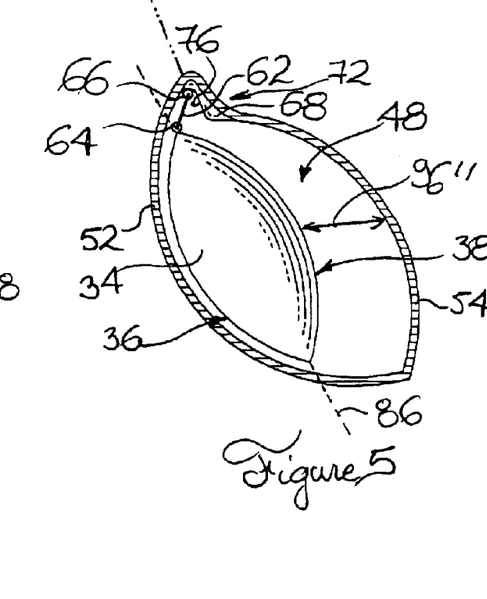
FIG. 5: in a partial cross sectional view with sections taken out, illustrates the intraocular lens implant shown in FIGS. 1 through 4 in a lens first position.

As illustrates more specifically in FIGS. 3 through 5, the shell segment joining edge (58) defines an intercepting geometrical plane (74) generally intercepting the latter. In situations wherein the shell component (44) is generally symmetrical, the intercepting geometrical plane (74) typically bisects the shell component (44). The abutment tongue (68) defines a corresponding abutment surface (76). The abutment surface (76), in turn, defines an abutment geometrical plane (78).

The abutment geometrical plane (78) typically extends at an intercepting-to-abutment plane angle (80) relative to the intercepting geometrical plane (74). Typically the intercepting-to-abutment plane angle (80) is such that the intercepting geometrical plane (74) intercepts the abutment geometrical plane (78) within the shell inner volume (48). Typically, although by no means exclusively, the intercepting-to-abutment plane angle has a value substantially in the range of 20°.

Referring now more specifically to FIG. 4, there is shown that the lens (34) typically defines a lens coupling region (84) located generally adjacent the first arm pivotal link (64) and a generally opposed distal segment (82). FIGS. 4 and 10 illustrate the lens (34) in an intermediate position between the lens first and second positions shown respectively in FIGS. 5, 11 and 3, 9. In the intermediate position shown in FIGS. 4 and 10, the distal segment (82) abuttingly contacts the inner surface (50) of the shell first wall segment (52). Preferably, the shell-to-lens coupling means further allows the lens coupling region (84) to be substantially stabilized when the lens (34) is in the lens intermediate position, shown in FIGS. 4 and 10. Preferably, the shell-to-lens coupling means allows a portion of the shell-to-lens coupling means to abuttingly contact the abutment surface (76) when the lens (34) is in both the lens second and intermediate positions shown respectively in FIGS. 3 and 4 and to be in a spaced relationship relative to the abutment surface (76) when the lens (34) is in the lens first position shown in FIG. 5.

Typically, the lens (34) forms a lens geometrical plane (86) generally intercepting the latter. In situations wherein the lens (34) is generally symmetrical, the lens geometrical plane (86) typically bisects the lens (34). The implanting support (42) is configured and sized so that the lens geometrical plane (86) is in a substantially parallel relationship with the abutment geometrical plane (78) when the lens (34) is in the lens intermediate position, shown in FIG. 4. Also, the implanting support (42) is configured and sized so that the lens geometrical plane (86) intercepts the abutment geometrical plane (78) when the lens (34) is the lens second geometrical planes shown respectively in FIGS. 3 and 9.

Figure 12:
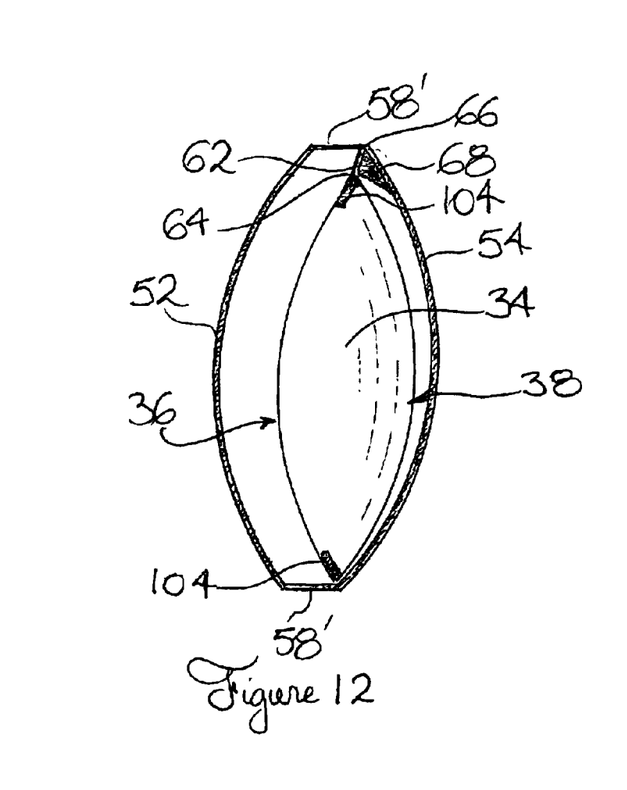
FIG. 12: in a partial cross sectional view with sections taken out, illustrates a intraocular lens implant in accordance with an alternative embodiment of the invention, the lens thereof being shown in a lens second position.
Figure 13:
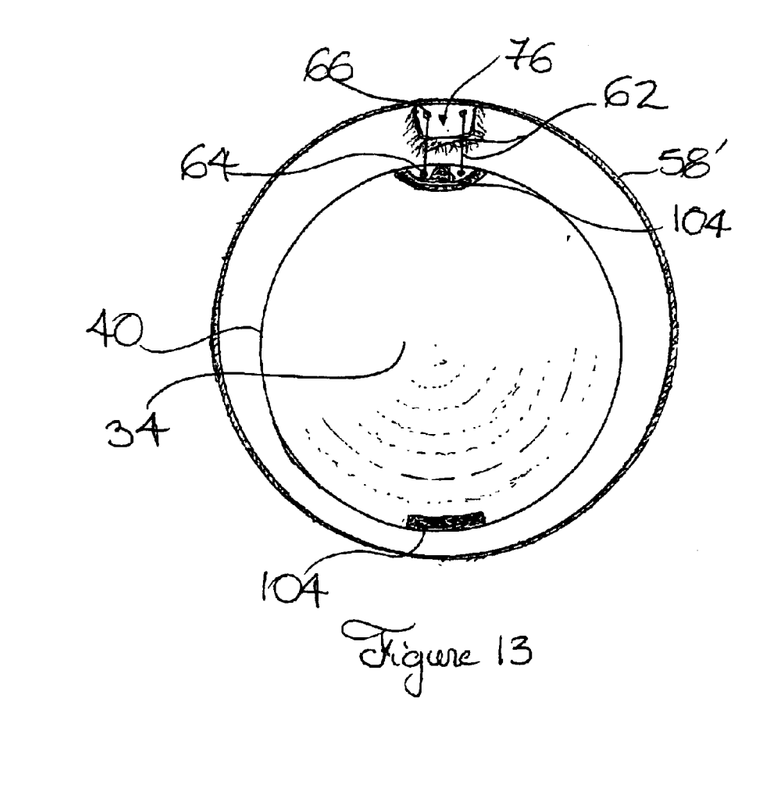
FIG. 13: in a front elevational view illustrates the intraocular lens implant shown in FIG. 12.
Figure 14:
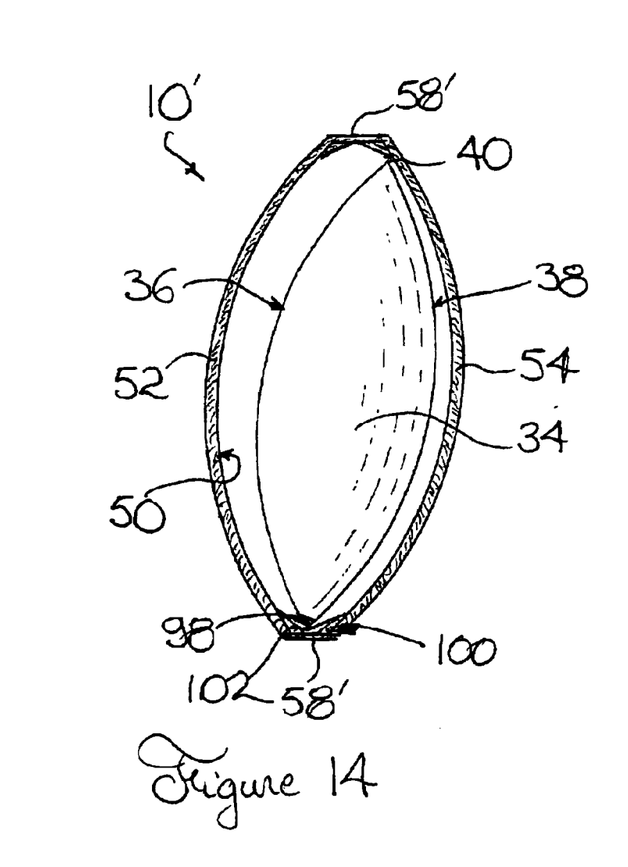
FIG. 14: in a partial cross sectional view with sections taken out, illustrates the an intraocular lens implant in accordance with an alternative embodiment of the invention, the implant being shown with a lens in a lens second position.
Figure 15:
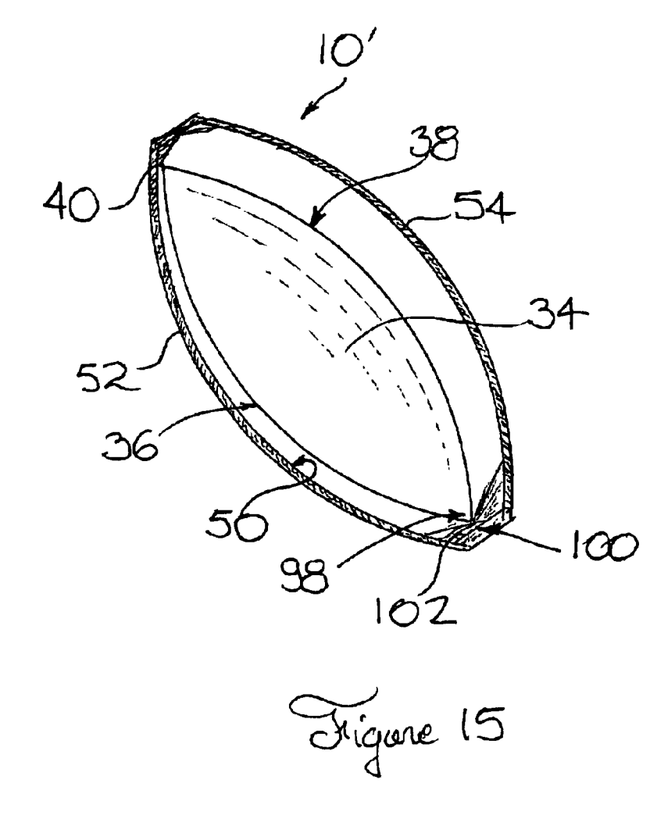
FIG. 15: in a partial cross sectional view with sections taken out, illustrates the intraocular lens implant shown in FIG. 14 in a lens first position.

As shown in FIGS. 12 and 13, the lens (34) is optionally provided with at least one and preferably two magnetizable or magnetized magnet components 104 embedded therein, mounted thereon or otherwise coupled thereto. The magnet components 104 are adapted to allow a magnet positioned outside the eye (12) to be used for displacing the lens (34) should the latter be stuck in an unwanted position or in situations wherein the wearer of the implant (10) wishes to look in a proximal visual field with the head thereof tilted rearwardly.

The shell cowponent (44) way be made out of any suitable and biocompatible material. For example, the shell component (44) could be made out of PMMA or any other suitable polymeric resin. Optionally, the shell component (44) could be made out of a resiliently deformable material to facilitate implantation thereof through a relatively small implantation aperture.

In use, the shell component (44) is typically implanted within the eye (12) so that the intercepting geometrical plane (74) forms an implanting angle (88) having a value substantially in range of 10° relative to a vertical axis (90). Movement of the head of the intended user causing movement of the lens (34) within the shell component (44) is adapted to provide accommodation to the eye of the intended user.

Figure 9:
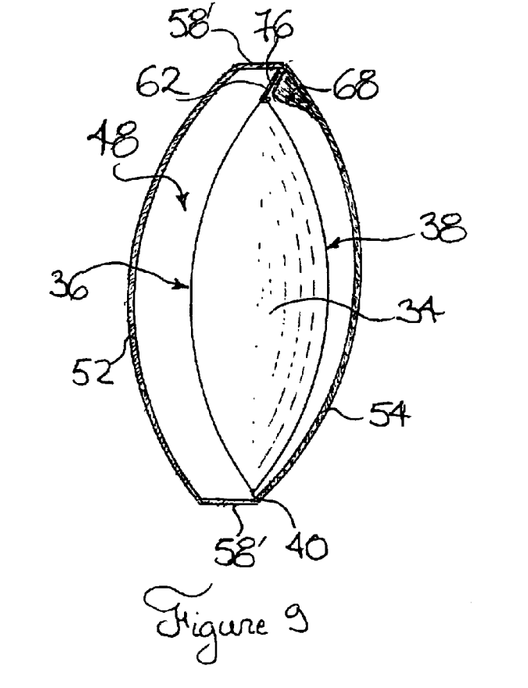
FIG. 9: in a partial cross sectional view with sections taken out, illustrates the an intraocular lens implant in accordance with an alternative embodiment of the invention, the implant being shown with a lens in a lens second position.
Figure 10:
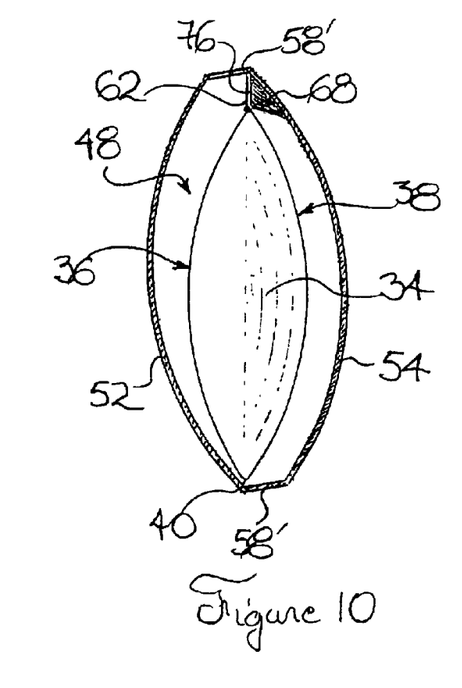
FIG. 10: in a partial cross sectional view with sections taken out, illustrates the intraocular lens implant shown in FIG. 9 in a lens intermediate position.
Figure 11:
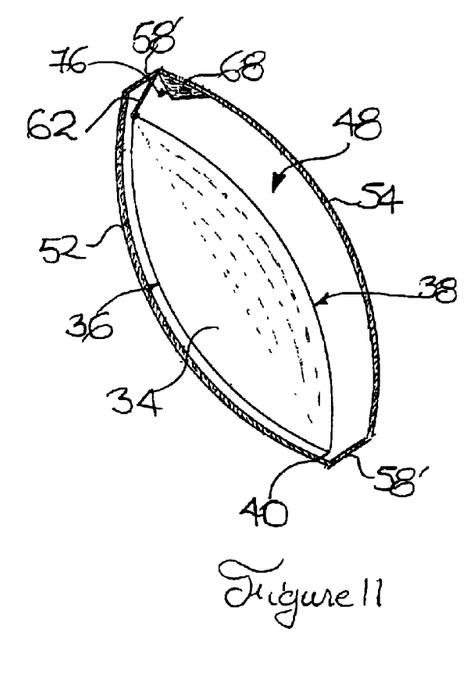
FIG. 11: in a partial cross sectional view with sections taken out, illustrates the intraocular lens implant shown in FIGS. 9 through 10 in a lens first position.

FIGS. 3 and 9, illustrate the relative positioning between the lens (34) and the shell component (44) when the head of an intended user is substantially vertically alligned position and the intended user is looking generally horizontally. In such a situation, the lens (34) is typically in the lens second position wherein the lens second surface (36) is in a proximal or abutting relationship relative to the peripheral wall second segment (54). The coupling arms (62) typically abuttingly contact the abutment surface (76) and are in a generally parallel relationship relative to the latter. The implantation angle (88) is adapted to ensure that the lens (34) remains in the lens first position despite decellarational forces or other factors acting thereon.

As the head of the intended user tilts frontwardly, the intercepting geometrical plane (74) is similarly pivoted according to arrow (92) in FIG. 4. Since the lens (34) hangs freely from the shell-to-lens coupling means, the distal segment (82) remains relatively stationary while the relative distance between the distal segment (82) and the inner surface of the peripheral wall first segment (52) decreases.

The spacing (94) between the distal segment (82) and the inner surface (50) of the peripheral wall first segment (52) decreases to a position wherein the distal segment (82) abuttingly contacts the inner surface (50) of the peripheral wall first segment (52). In such a position referred to as the lens intermediate position, shown in FIGS. 4 and 10, the distal segment (82) of the lens (34) is stabilized by the abutting contact between the distal segment (82) and the peripheral wall first segment (52) while the lens coupling region (84) is stabilized by the abutting relationship between the shell-to-lens coupling means and the abutment surface (76).

The intraocular implant (10) hence provides an intermediate lens position wherein the lens (34) is substantially, and at least partially stabilized and wherein the convex power of the lens (34) is increased by the augmentation of the spacing (96). Typically, the lens (34) and shell component (44) are configured and sized so that abutment of the distal segment (82) occurs when the pivotal movement of the shell component (44) reaches an angular value substantially in the range of the intercepting-to-abutment plane angle (80).

Once the lens (34) has reached the lens intermediate position shown in FIGS. 4 and 10, further forward tilting of the head of the intended user causes the distal segment (82) to act as a contacting area or pivot for allowing the lens coupling region (84) to pivot forwardly. As the lens coupling region (84) pivots forwardly, the shell-to-lens coupling means becomes spaced relative to the abutment surface (76) and the lens (34) eventually reaches the lens first position shown in FIGS. 5 and 11 wherein the lens first surface (36) is in a generally proximal or abutting relationship relative to the inner surface of the peripheral wall first segment (52). The spacing (96") being further increased, the convex power of the lens (34) is also increased thus providing further accommodation.

Hence, the intraocular implant (10) provides at least three different lens positions wherein the lens (34) is substantially stabilized and offers a generally predetermined degree of accommodation. In the lens first and second position, the lens first and second surfaces (36), (38) are preferably in a generally complimentary mating relationship relative to the inner surface (50) of the peripheral wall first and second segments (52), (54) so as to reduce the risk of refraction. The lens offers progressive accommodation through movement of the distal end coupling regions (82), (84) of the lens relative to the shell component (44).

Since the lens moves within the shell and since the latter remains relatively stable, accommodation is achieved with minimal interference with surrounding intraocular structures. Also, since friction is reduced between the lens (34) and its surrounding environment, accommodation is performed through a generally smooth and relatively quick movement of the lens (34).

Still furthermore, in the event that the shell-to-lens coupling means becomes damaged or otherwise altered, the lens (34) will remain within the shell component (44) and may still provide for some degree of accommodation by allowing the lens (34) to contact the inner surface of the shell peripheral wall adjacent the base thereof allowing the distal segment (82) to act as a pivot.

Referring now more specifically to FIG. 10, there is shown an intraocular implant (10') in accordance with an alternative embodiment of the invention. The intraocular implant (10') is substantially similar to the intraocular implant (10) shown in FIGS. 1 through 9 and, hence, similar reference numerals will be used to denote similar components. One of the main differences between the intraocular implant (10') and the hereinabove disclosed intraocular implant (10) resides in that the intraocular implant (10') is deprived of coupling arms (62) and corresponding first and second arm pivotal links (64), (66). The lens (34) of the intraocular implant (10') typically rests at the bottom or base of the shell component (44) and is typically free to rotate about its center axis. The lens peripheral edge (40) defines a lens edge pivot portion (98).

Similarly, the shell segment joining edge (58) defines a corresponding shell edge pivot portion (100). The lens and shell edge pivot portions (98), (100) are complementarily configured and sized so that when the lens (34) abuttingly rests against the peripheral wall inner surface (50), the lens and shell edge pivot portions (98), (100) interact with each other for allowing the lens (34) to pivot between the lens first and second positions illustrated respectively in FIGS. 14 and 15.

Optionally, the intraocular implant (10') may be further provided with a lens stabilizing means for at least partially stabilizing the lens (34) in a lens intermediate position between the lens first and second positions wherein the lens first and second surfaces (36), (38) are both in a spaced relationship relative to the shell wall first and second wall segments (52), (54).

The lens stabilizing means typically includes a stabilizing protrusion (102) extending from the shell edge pivot portion. The stabilizing protrusion (102) is configured and sized for receiving and releasably retaining the lens pivot portion (98) so that the lens (34) is releasably stabilized in the lens intermediate position.

The embodiments of the invention in which an exclusive privilege or property is claimed are defined as follows:

1. An intraocular implanting support for movably supporting a lens and allowing said lens to be implanted within an eye, said lens including a lens body defining a lens first surface, a generally opposed lens second surface and a lens peripheral edge extending substantially peripherally therebetween, said implanting support comprising:

a shell component said shell component including a shell peripheral wall, said shell peripheral wall at least partially encompassing a shell inner volume for protectively receiving said lens and allowing the latter to move therein;

a shell-to-lens coupling means extending between said shell component and said lens for coupling said shell component to said lens and allowing said lens to move within said shell inner volume according to a generally predetermined pattern upon movement of said shell component said shell-to-lens coupling means allowing said lens to be pivotally coupled to said shell component for pivotal movement relative to said shell component between lens accommodating positions;

said shell peripheral wall enclosing said shell inner volume for protectively separating the external environment located outside said shell peripheral wall;

said shell inner volume being at least partially vacuumed.

2. An intraocular implanting support for movably supporting a lens and allowing said lens to be implanted within an eye, said lens including a lens body defining a lens first surface, a generally opposed lens second surface and a lens peripheral edge extending substantially peripherally therebetween, said implanting support comprising:

a shell component, said shell component including a shell peripheral wall, said shell peripheral wall at least partially encompassing a shell inner volume for protectively receiving said lens and allowing the latter to move therein;

a shell-to-lens coupling means extending between said shell component and said lens for coupling said shell component to said lens and allowing said lens to move within said shell inner volume according to a generally predetermined pattern upon movement of said shell component; said shell-to-lens coupling means allowing said lens to be pivotally coupled to said shell component for pivotal movement relative to said shell component between lens accommodating positions;

said shell peripheral wall enclosing said shell inner volume for protectively separating the external enuironment located outside said shell peripheral wall;

said shell peripheral wall defining a shell wall first segment and a shell wall second segment, the inner surface of both said shell wall first and second segments having a generally concave configuration;

said shell first and second wall segments being joined together about a common and generally peripheral shell segment joining edge; inwardly into said shell inner volume from a predetermined quadrant of said shell second wall segment adjacent said shell segment joining edge.

3. An implanting support as recited in claim 2 wherein said shell segment joining edge defines an intercepting geometrical plane generally intercepting the latter, said abutment tongue defining an abutment surface, said abutment surface defining an abutment geometrical plane, said abutment geometrical plane extending at an intercepting-to-abutment plane angle relative to said intercepting geometrical plane.

4. An implanting support as recited in claim 3 wherein said intercepting-to-abutment plane angle is such that said intercepting geometrical plane intercepts said abutment geometrical plane within said shell inner volume.

5. An implanting support as recited in claim 2 wherein said lens peripheral edge is pivotally attached to said shell wall inner surface generally adjacent said shell segment joining edge for allowing said lens to pivot between a lens first position wherein said lens is in a substantially proximal relationship relative to said shell wall first segment and a lens second position wherein said lens is in a substantially proximal relationship relative to said shell wall second segment; said shell-to-lens coupling means including at least one coupling arm pivotally attached between said lens and said shell wall inner surface;

said coupling arm being pivotally attached to said lens adjacent a lens coupling region and to said shell wall inner surface respectively by a first arm pivotal link and by a second arm pivotal link; said shell segment joining edge defining an intercepting geometrical plane generally intercepting the latter, said abutment tongue defining an abutment surface, said abutment surface defining an abutment geometrical plane, said abutment geometrical plane extending at an intercepting-to-abutment plane angle relative to said intercepting geometrical plane; said shell-to-lens coupling means allowing said lens coupling region to be substantially stabilized when said lens is in a lens intermediate position between said lens first and second positions wherein a distal segment of said lens located generally opposite said lens coupling region abuttingly contacts said shell first wall segment.

6. An implanting support as recited in claim 5 wherein said shell-to-lens coupling means allows a portion of said shell-to-lens coupling means to abuttingly contact said abutment surface when said lens is in both said lens second and intermediate positions and to be in a spaced relationship relative to said abutment surface when said lens is in said lens first position.

7. An implanting support as recited in claim 6 wherein said lens forms a lens geometrical plane substantially bisecting said lens, said implanting support being configured and sized so dint said lens geometrical plane is in a substantially parallel relationship with said abutment geometrical plane when said lens is in said lens intermediate position and wherein said lens geometrical plane intercepts said abutment geometrical planer when said lens is in both said lens first and second geometrical planes.

8. An intraocular implant comprising:
a lens, said lens including a lens body defining a lens first surface, a generally opposed lens second surface and a lens peripheral edge extending substantially peripherally therebetween;
a shell component said shell component including a shell peripheral wall, said shell peripheral wall defining a peripheral wall inner surface, said shell peripheral wall encompassing a shell inner volume for protectively enclosing said lens and allowing the latter to move therein between lens accommodating positions;

a shell-to-lens coupling means extending between said shell component and said lens for coupling said shell component to said lens and allowing said lens to move within said shell inner volume according to a generally predetermined pattern upon movement of said shell component said shell-to-lens coupling means allowing said lens to be pivotally coupled to said shell component for pivotal movement relative to said shell component between lens accommodating positions;

said lens and shell components being complimentarily configured and sized so as to allow said lens to pivot within said shell inner volume for varying the spacing between said lens first and second surfaces and said peripheral wall inner surface;

said shell peripheral wall defining a shell wall first segment and a shell wall second segment, said shell first and second wall segments both having a generally cupolaed configuration, said shell first and second wall segments being joined together in a generally opposed relationship relative to each other about a common and generally peripheral shell segment joining edge so as to form a generally externally biconvex and internally biconcave shell peripheral wall; said lens being pivotable within said shell inner volume between a lens first position wherein said lens is in a substantially proximal relationship relative to said shell wall first segment and a lens second position wherein said lens is in a substantially proximal relationship relative to said shell wall second segment;

said intraocular implant further comprising a shell-to-lens coupling means extending between said shell component and said lens for coupling said shell component to said lens and allowing said lens to move between said shell first and second positions; said shell-to-lens coupling means includes at least one coupling arm pivotally attached between said lens and said shell wall inner surface;

said coupling arm being pivotally attached to said lens by a first arm pivotal link and said coupling arm in pivotally attached to said shell wall inner surface by a second arm pivotal link;

an abutment tongue protuding inwardly into said shell inner volume from a predetermined quadrant of said shell second wall segment adjacent said shell segment joining edge.

9. An intraocular implant as recited in claim 8 wherein said shell segment joining edge defines an intercepting geometrical plane generally intercepting the latter; said abutment tongue defining an abutment surface, said abutment surface defining an abutment geometrical plane, said abutment geometrical plane extending at an intercepting-to-abutment plane angle relative to said intercepting geometrical plane; said shell-to-lens coupling means allowing said lens coupling region so be substantially stabilized when said lens is in a lens intermediate position between said lens first and second positions wherein a distal segment of said lens located generally opposite said lens coupling region abuttingly contacts said shell first wall segment.

* * * * *